US011046995B2

(12) United States Patent
Crawford et al.

(10) Patent No.: US 11,046,995 B2
(45) Date of Patent: Jun. 29, 2021

(54) METHOD FOR FINDING LOW ABUNDANCE SEQUENCES BY HYBRIDIZATION (FLASH)

(71) Applicant: The Regents of the University of California, Oakland, CA (US)

(72) Inventors: Emily D. Crawford, San Francisco, CA (US); Eric D. Chow, Richmond, CA (US); Joseph L. DeRisi, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 220 days.

(21) Appl. No.: 16/315,975

(22) PCT Filed: Aug. 14, 2017

(86) PCT No.: PCT/US2017/046821
§ 371 (c)(1),
(2) Date: Jan. 7, 2019

(87) PCT Pub. No.: WO2018/035062
PCT Pub. Date: Feb. 22, 2018

(65) Prior Publication Data
US 2019/0300935 A1 Oct. 3, 2019

Related U.S. Application Data

(60) Provisional application No. 62/375,789, filed on Aug. 16, 2016.

(51) Int. Cl.
| *C12Q 1/6806* | (2018.01) |
| *C12N 15/10* | (2006.01) |
| *C12N 9/22* | (2006.01) |
| *C12N 15/11* | (2006.01) |
| *C12Q 1/6855* | (2018.01) |
| *C12Q 1/6869* | (2018.01) |

(52) U.S. Cl.
CPC ............. *C12Q 1/6806* (2013.01); *C12N 9/22* (2013.01); *C12N 15/10* (2013.01); *C12N 15/11* (2013.01); *C12Q 1/6855* (2013.01); *C12Q 1/6869* (2013.01); *C12N 2310/20* (2017.05)

(58) Field of Classification Search
CPC ...... C12Q 1/68; C12Q 1/6806; C12Q 1/6855; C12Q 1/6869
See application file for complete search history.

(56) References Cited

U.S. PATENT DOCUMENTS

| 5,508,169 A * | 4/1996 | Deugau ................ C12Q 1/6855 435/6.1 |
| 2009/0042196 A1 | 2/2009 | Guo |
| 2010/0112588 A1* | 5/2010 | Farinas ................ C12Q 1/6869 435/6.12 |
| 2011/0059864 A1* | 3/2011 | Farinas ................ C12Q 1/6872 506/12 |
| 2014/0356867 A1* | 12/2014 | Peter .................... C12Y 301/00 435/6.11 |
| 2015/0031552 A1 | 1/2015 | Gao et al. |
| 2015/0225773 A1 | 8/2015 | Farmer et al. |
| 2016/0138081 A1 | 5/2016 | Fujii et al. |
| 2016/0208241 A1 | 7/2016 | Tsai et al. |
| 2016/0312267 A1* | 10/2016 | Otwinowski ........ C12Q 1/6806 |
| 2017/0081702 A1* | 3/2017 | Dahl ...................... C12Q 1/682 |
| 2018/0051320 A1* | 2/2018 | DeRisi ................ C12Q 1/6848 |
| 2018/0216163 A1* | 8/2018 | Willey ................ C12Q 1/6806 |
| 2019/0300935 A1* | 10/2019 | Crawford ............. C12Q 1/6806 |
| 2019/0338362 A1* | 11/2019 | Tam ....................... G16B 40/00 |

FOREIGN PATENT DOCUMENTS

| WO | WO2016037389 | 3/2016 |
| WO | 2016/100955 A2 * | 6/2016 |
| WO | WO2017044843 | 3/2017 |
| WO | WO2017059313 | 4/2017 |
| WO | WO2019224560 | 11/2019 |
| WO | 2020/033438 A1 * | 2/2020 |

OTHER PUBLICATIONS

Allen et al., J. of Forensic Science 43(3) : 453-464 (Year: 1998).*
Jones M., J. of Archaeological Science 30 :629-635 (Year: 2003).*
Gibellini et al., J. of Clinical Microbiology 29:282-289 (Year: 2004).*
Tringe et al., Science 6:805 (Year: 2005).*
Meyer et al., Nucleic Acids Research 35(15) : e97 (Year: 2007).*
Craig et al., Nature Methods 5(10) : 887 (Year: 2008).*
Meyer et al., Cold Spring Harb Protoc. 2010 (6) : Jun. (Year: 2010).*
Segata et al., Genome Biology 13:R42 (Year: 2012).*
Gade et al., Eukaryotic Cell 12(5) : 677 (Year: 2013).*
Henrich et al., J. of Virological Methods 186: 68-72 (Year: 2013).*
Hilhorst et al.BMC Nephrology 14 :238 (Year: 2013).*
Kato et al., J. of Clinical Microbiology 51(1) : 314-317 (Year: 2013).*
Ross et al., PLOSlone 8(9) : e73056 (Year: 2013).*
Devault et al., Scientific Reports 4:4245 (Year: 2014).*
Gupta et al., The J. of Clinical In Investigation 124(10) :4154 (Year: 2014).*

(Continued)

Primary Examiner — Ethan C Whisenant
(74) Attorney, Agent, or Firm — James S. Keddie; Bozicevic, Field & Francis LLP

(57) ABSTRACT

A method of sample analysis is provided. In some embodiments, the method comprises: (a) digesting a mixed nucleic acid sample with a plurality of reprogrammed nucleic acid-directed endonucleases that target sequences of interest to produce a digested sample, wherein at least some of the fragments in the digested sample comprise: (i) a sequence of interest and (ii) at least one ligatable end that has been generated by endonuclease cleavage; (b) enriching for fragments that contain the sequence of interest; and (c) analyzing the enriched fragments. Kits for performing the method are also provided.

20 Claims, 4 Drawing Sheets

Specification includes a Sequence Listing.

(56) References Cited

OTHER PUBLICATIONS

Gao et al., "Insights into Disease-Associated Mutations in the Human Proteome through Protein Structural Analysis", Structure, 2015, 23: 1362-1369.

Gu, et al. "Depletion of Abundant Sequences by Hybridization (DASH): using Cas9 to remove unwanted high-abundance species in sequencing libraries and molecular counting applications", Genome Biol., 2016, 17:41, pp. 1-13.

Hegele, "SNP Judgments and Freedom of Association", Arteriosclerosis, Thrombosis, and Vascular Biology, 2002, 22:1058-1061.

Hindson et al., "High-Throughput Droplet Digital PCR System for Absolute Quantitation of DNA Copy Number", Analytical Chemistry, 2011, 83: 8604-8610.

Hsu et al., "DNA targeting specificity of RNA-guided Cas9 nucleases", Nature Biotechnology, 2013, 31(9): 827-832.

Jansen et al., "Discovery and functional prioritization of Parkinson's disease candidate genes from large-scale whole exome sequencing", Genome Biology, 2017, 18(22): pp. 1-26.

Kloss-Brandstatter et al., "Somatic Mutations throughput the Entire Mitochondria Genome are Associated with Elevated PSA Levels in Prostate Cancer Patients", The American Journal of Human Genetics, 2010, 87: 802-812.

Mardis, "Next-Generation DNA Sequencing Methods", Annual Review of Genomics and Human Genetics, 2008, 9:387-402.

McCarthy et al., "Human disease genomics: from variants to biology", Genome Biology, 2017, 18(20):1-3.

Ramani, et al. "Smash and Dash with Cas9", Genome Biol., 2016, 17:42, pp. 1-3.

Quan et al., "FLASH: a next-generation CRIPSR diagnostic for multiplexed detection of antimicrobial resistance sequence", Nucleic Acids Research, 2019, 47(14):e83.

Ukai et al., "A new technique to prevent self-ligation of DNA", Journal of Biotechnology, 2002, 97(3):233-242.

\* cited by examiner

METHOD FOR FINDING LOW ABUNDANCE SEQUENCES BY HYBRIDIZATION (FLASH)

CROSS-REFERENCING

This application is a §371 national phase of International Application No. PCT/US2017/046821, filed on Aug. 14, 2017, which claims the benefit of U.S. provisional application Ser. No. 62/375,789, filed on Aug. 16, 2016, which applications are incorporated by reference herein.

BACKGROUND

Current methods for enriching low-abundance sequences in a complex nucleic acid library often involve either multiplex PCR or hybridization to labeled oligonucleotides. Both of these method can be inefficient, difficult to implement, expensive to optimize, and limited in the number of sequences that can be enriched for in a given sample.

There is a constant need for new methods for enriching for low abundance sequences in a nucleic acid sample.

SUMMARY

Described herein is a method referred to as Finding Low Abundance Sequences by Hybridization, or "FLASH", a technique that uses a sequence-specific nuclease, such as CRISPR/Cas9, to cut specific sites of interest in a DNA library or other sample prior to sequencing or other molecular counting applications. In some implementations, the newly exposed ends of the DNA are then free to be ligated to specific adapter sequences that allow them to be amplified. In these embodiments, a single PCR step using only a pair of primers specific to the adaptors can therefore amplify hundreds, thousands, or possibly millions of different sequences, in a fully programmable way. In some cases, to reduce sequencing of non-targeted molecules, the ends of the DNA molecules in the DNA source may be blocked, e.g., treated with a phosphatase or using another method prior to nuclease digestion to block any already accessible DNA ends.

In some embodiments, the method may comprise: (a) digesting a end-blocked (e.g., phosphatase-treated) mixed nucleic acid sample with a plurality of reprogrammed nucleic acid-directed endonucleases that target sequences of interest to produce a digested sample, wherein at least some of the fragments in the digested sample comprise: (i) a sequence of interest and (ii) at least one ligatable end that has been generated by endonuclease cleavage; (b) enriching for fragments that contain the sequence of interest; and (c) analyzing the enriched fragments.

Kits for performing the method are also provided.

BRIEF DESCRIPTION OF THE DRAWINGS

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
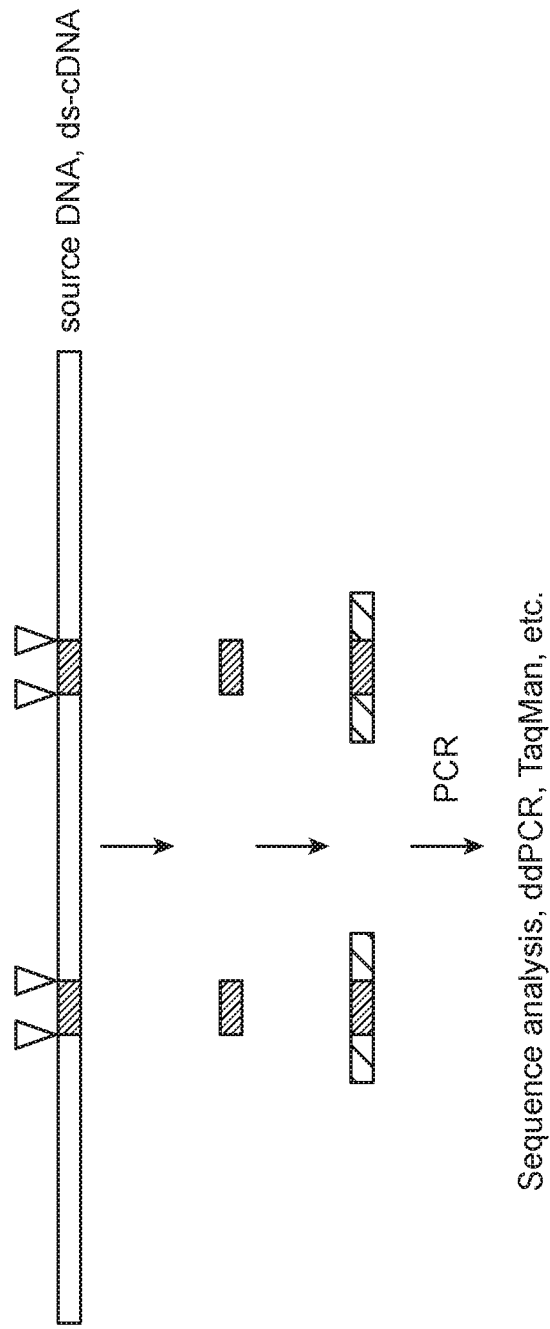
FIG. 1 shows some of the principles of the FLASH method.
Figure 2:
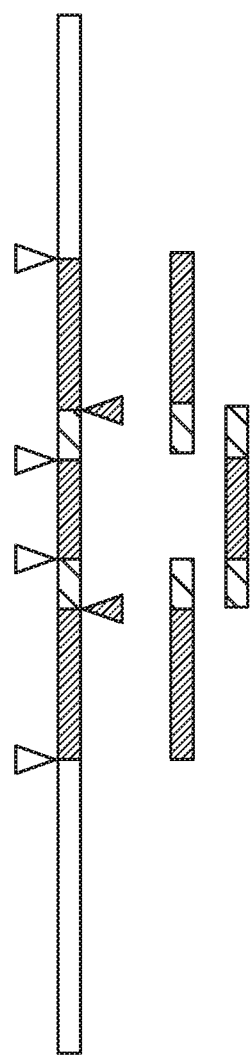
FIG. 2 shows how different FLASH pools (denoted by open and filled triangles) can be used to fragment desired DNA fragments (filled bars) with overlapping fragments. Different FLASH pools (denoted by open and filled triangles) can be used to fragment desired DNA fragments (filled bars) with overlapping fragments (hashed bars). The overlap regions can be targeted towards SNPs, translocations, or regions flanking repeat sequences. These overlapping fragments can be combined before library preparation and then used to assemble sequencing reads.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. The nucleic acid samples used herein may be complex in that they contain multiple different molecules that contain sequences. Genomic DNA and cDNA made from mRNA from a mammal (e.g., mouse or human) are types of complex samples. Complex samples may have more than $10^4$, $10^5$, $10^6$ or more than $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, an FFPE sample, a clinical, environmental, or other type of sample may be employed herein.

The term "nucleic acid sample," as used herein denotes a sample containing nucleic acids. A nucleic acid sample used herein may be complex in that they contain multiple different molecules that contain sequences. Genomic DNA, RNA (and cDNA made from the same) from a mammal (e.g., mouse or human) are types of complex samples. Complex samples may have more than $10^4$, $10^5$, $10^6$ or more than $10^7$ different nucleic acid molecules. A target molecule may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., peptide nucleic acid or PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18 to 40, 20 to 35, 21 to 30 nucleotides long, and any length between the stated ranges. Typical primers can be in the range of between 10 to 50 nucleotides long, such as 15 to 45, 18 to 40, 20 to 30, 21 to 25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "genomic region", as used herein, refers to a region of a genome, e.g., an animal or plant genome such as the genome of a human, monkey, rat, fish or insect or plant.

The term "genomic sequence," as used herein, refers to a sequence that occurs in a genome.

The term "genomic fragment," as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment, or to at least the 5' end of a molecule), or may not be adaptor ligated.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pacific Biosciences and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence", "molecular barcode" or "index", as used herein, refers to a unique sequence of nucleotides used to (a) identify and/or track the source of a polynucleotide in a reaction and/or (b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide, or both the 5' end and the 3' end. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term "adjacent to" refers to a distance of less than the longest dimension of a nucleotide. The term "ligatably adjacent to" means that two nucleotides are immediately adjacent to one another on a strand with no intervening nucleotides.

The term "tailed", in the context of a tailed primer or a primer that has a 5' tail, refers to a primer that has a region (e.g., a region of at least 12-50 nucleotides) at its 5' end that does not hybridize to the same target as the 3' end of the primer.

The term "distinguishable sequences" refers to sequences that are different to one another.

The term "target nucleic acid" as use herein, refers to a polynucleotide of interest under study.

The term "target nucleic acid molecule" refers to a single molecule that may or may not be present in a composition with other target nucleic acid molecules. An isolated target nucleic acid molecule refers to a single molecule that is present in a composition that does not contain other target nucleic acid molecules.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "adaptor" refers to a nucleic acid that can be joined, via a ligase mediated reaction, to at least one strand of a double-stranded DNA molecule. In one embodiment, an adaptor may be a Y-adaptor. As would be apparent, one end of an adaptor may be designed to be compatible with overhangs made by cleavage by a endonuclease, e.g., it may have blunt ends or a 5' T overhang. The term "adaptor" refers to molecules that are at least partially double-stranded.

An adaptor may be 40 to 150 bases in length, e.g., 50 to 120 bases, although adaptors outside of this range are envisioned.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation. Each strand of an adaptor-tagged double-stranded DNA that has been ligated to a Y adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

The term "universal adaptor" refers to an adaptor that is ligated to both ends of the nucleic acid molecules under study. In certain embodiments, the universal adaptor may be a Y-adaptor. Amplification of nucleic acid molecules that have been ligated to Y-adaptors at both ends results in an asymmetrically tagged nucleic acid, i.e., a nucleic acid that has a 5' end containing one tag sequence and a 3' end that has another tag sequence.

The term "adaptor-tagged," as used herein, refers to a nucleic acid that has been tagged by an adaptor. The adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation.

As used herein, the term "separately digesting" refers to two or more different cleavage reactions.

As used herein, the term "nucleic acid guided endonuclease" refers to DNA- and RNA-guided endonucleases including the Argonaut and the Type II CRISPR/Cas-based system that is composed of two components: a nuclease (e.g., a Cas9 endonuclease or variant or ortholog thereof) that cleaves the target DNA and a guide RNA (gRNA) that targets the nuclease to a specific site in the target DNA. See, e.g., Hsu et al (Nature Biotechnology 2013 31: 827-832).

As used herein, the term "portion" refers to a part (e.g., an aliquot) of a sample.

As used herein, the term, "defined site" refers to a selected sequence.

As used herein, the term, "selectively amplifying" refers to an amplification reaction (e.g., a PCR reaction) in which only chosen sequences are amplified.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

As used herein, the term "biotin moiety" refers to an affinity agent that includes biotin or a biotin analogue such as desthiobiotin, oxybiotin, 2-iminobiotin, diaminobiotin, biotin sulfoxide, biocytin, etc. Biotin moieties bind to streptavidin with an affinity of at least 10-8 M. A biotin affinity agent may also include a linker, e.g., -LC-biotin, -LC-LC-Biotin, -SLC-Biotin or -PEGn-Biotin where n is 3-12.

The terms "affinity tag" and "capture moiety" refer to moieties that are capable of: a) specifically binding to one other non-covalently or b) selectively reacting one another to form a covalent bond. Examples of pairs of suitable affinity tags and capture agents that specifically bind to one another non-covalently are numerous and include, but are not limited to: streptavidin/avidin, digoxigenin/anti-digoxigenin antibody, fluorescein/anti-fluorescein antibody, although many others are known. Examples of chemoselective reactive groups that selectively react with one another to form a covalent bond are numerous and include: amines and active esters such as an NHS esters, thiols and maleimide or iodoacetamide), as well as groups that can react with one another via Click chemistry, e.g., azide and alkyne groups. Ribonucleotides that contain affinity tags that can be used herein are available commercially from many sources.

The term "end-blocked" refers to an end that has been modified to make is unavailable for ligation. A nucleic acid may be end blocked by treatment with a phosphatase although other methods can be used.

DETAILED DESCRIPTION

In some embodiments, the method may comprise digesting a mixed nucleic acid sample (i.e., a nucleic acid sample that contains DNA from at least two sources, where the DNA from one sources may represent less than 10%, less then 5%, less than 2% or less than 1% of the total DNA in the sample) with a plurality of reprogrammed nucleic acid-directed endonucleases that target sequences of interest (i.e., a set of Cas9 endonuclease, Argonaut, ortholog or variant of the same that have synthetic guide RNAs or DNAs that target the endonucleases to pre-determined target sites in a target nucleic acid, e.g., a target genome). This step produces a digested sample that contains fragments of the nucleic acid in the sample, where at least some of the fragments in the digested sample contain: (i) a sequence of interest and (ii) at least one ligatable end that has been generated by endonuclease cleavage (i.e., an end that contains a 5' phosphate and a 3' hydroxyl, where the end is blunt or has a defined overhang). Some nucleic acid-directed endonucleases, including Cas9, generates blunt ends, whereas others produce may produce defined overhangs. After digestion, fragments that contain the sequence of interest can be enriched, e.g., using size selection, by ligating an adaptor that comprises a capture moiety (e.g., a biotin moiety) to the ligatable end generated by the endonuclease, binding the capture moiety to a support (e.g., a streptavidin support), and washing away the unbound nucleic acid, or by ligating adaptors (e.g., "Y-adaptors") to the ends of the fragments and amplifying the ligated fragments by PCR using primers that bind to or are complementary to sequences in the Y adaptors. The enriched fragments can be analyzed by any suitable method, e.g., sequencing.

For Cas9 the guide RNAs may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a sgRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas 9 protein, or only one or some of the functions, including binding activity, and nuclease activity.

For Cas9 to successfully bind to DNA, the target sequence in the genomic DNA should be complementary to the gRNA sequence and must be immediately followed by the correct protospacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type II CRISPR system is derived from *S. pyogenes* and the PAM sequence is NGG located on the immediate 3' end of the gRNA recognition sequence. The PAM sequences of Type II CRISPR systems from exemplary bacterial species include: *Streptococcus pyogenes* (NGG), *Neisseria meningitidis* (NNNNGATT), *Streptococcus thermophilus* (NNAGAA) and *Treponema denticola* (NAAAAC). With some other sequence-specific nucleases, such as Argonauts, a PAM site is not required for binding and cutting the target DNA.

As would be apparent, this reaction may be done in vitro, i.e., in a cell-free environment using isolated nucleic acid (e.g., isolated DNA). The mixed sample may be collected from any source, including any organism, organic material or nucleic acid-containing substance including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human.

The guide RNAs used in the method may be designed so that they direct binding of the endonuclease to pre-determined cleavage sites in a target genome, for example. In certain cases, the cleavage sites may be chosen so as to release a fragment that contains a region of unknown sequence, or a region containing a SNP, nucleotide insertion, nucleotide deletion, rearrangement, etc. Since genomic isolation methods, and the nucleotide sequences of many organisms (including many bacteria, fungi, plants and animals, e.g., mammals such as human, primates, and rodents such as mouse and rat) are known, designing guide RNAs for use in the present method should be within the skill of one of skilled in the art. For example, Cas9-gRNA complexes can be programmed to bind to any sequence, provided that the sequence has a PAM motif. In theory, the Cas9-gRNA complexes could cleave the genomic DNA to produce fragments in the range of 30-50 bp. However, in practice, the minimal interval between the cleavage sites may be e.g., in the range of 50-900 bp. In some embodiments, the sgRNA or crRNA can be a degenerate sequence to target relatively conserved regions.

The method may make use of a set of at least 2, at least 5, at least 10, at least 100, at least 1,000, at least 10,000, at least 50,000 or at least 100,000 or more different guide RNAs/DNAs that are each complementary to a different, pre-defined, site in one or more genome. The distance between neighboring sites may vary greatly depending on the desired application. In some embodiments, the distance between neighboring sites may be in the range of 100 bp to 200 kb, and, in particular embodiments, the sites may be chosen to release fragments that are within a defined, size range, e.g., 100 bp to 2 kb, e.g., 200 bp to 1 kb for example, or larger (e.g., 500 bp to 20 kb) for nanopore and/or PacBio sequencing. In certain cases, the guide RNAs/DNAs may be may be chosen to release fragments that are of a size (e.g., less than 1 kb or less than 500 bp) that are suitable for size selection. In these embodiments, the fragments may be less than 1 kb in length or longer than about 1 kb in length and the enriching may be done by size selecting the fragments.

In some embodiments, digestion by the endonuclease may produce fragments that have two ends, both of which are ligatable. In these embodiments, the method comprises ligating adaptors to both ends of the fragments, thereby allowing the ligated fragments to be enriched by PCR using a single pair of primers that hybridize to the adaptors, or complements thereof. In these embodiments, the fragments can also be enriched by size, before or after they are ligated to the adaptors. As would be apparent, the adaptor used should be compatible with the ends generated by the endonuclease. In some embodiments, the end of the adaptor that is ligated to the fragments may be blunted ended. In other embodiments, the end of the adaptor that is ligated to the fragments may have an overhang that is complementary to the overhang generated by the endonuclease. In further embodiments, blunt-ended fragments may be A-tailed (e.g., using Taq polymerase) prior to ligation to a T-tailed adaptor. As noted above, in some embodiments, the adaptor may be a Y-adaptor and, as such, each strand of a ligation product may by asymmetrically tagged in that it has the sequence of one strand of the Y-adaptor at one end and the other strand of the Y-adaptor at the other end, where the added sequences are not the same or complementary. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

In some embodiments, the adaptor may contain an index sequence, e.g., a sequence that varies from molecule to molecule, such as a random sequence, thereby allowing molecules to be counted. In these embodiments, the method may comprises ligating an indexed adaptor to both ends of the fragments, amplifying the ligated fragments, sequencing the ligated fragments to produce sequence reads, and then counting the number of molecule indexer sequences that are associated with a sequence of interest in the sequence reads, thereby provide an estimate of the copy number of the sequence of interest in the nucleic acid sample. This allows the user to evaluate the relative quantities of different sequence molecules in the original sample.

The method may be used to obtain overlapping sequence reads, thereby allowing assembly of a contig. In these embodiments, the method may comprise: (a) separately digesting (e.g., in separate containers): (I) a first portion of the mixed nucleic acid sample with a first plurality of reprogrammed nucleic acid-directed endonucleases that target sequences of interest to produce a first digested sample, wherein at least some of the fragments in the digested sample comprise: (i) a first sequence of interest and (ii) at least one ligatable end that has been generated by endonuclease cleavage; (II) a second portion of the mixed nucleic acid sample with a second plurality of reprogrammed nucleic acid-directed endonucleases that target sequences of interest to produce a second digested sample, wherein at least some of the fragments in the digested sample comprise: (i) a second sequence of interest and (ii) at least one ligatable end that has been generated by endonuclease cleavage. In this method, the endonucleases in each digestion may be designed so that at least some of the fragments in the first digested sample overlap with at least some of the fragments in the second digested sample, e.g., may have an overlap of at least 50, at least 100 or at least 200 bases). The fragments that contain the sequence of interest may be enriched as described above (e.g., by ligating an adaptor and amplifying the fragments by PCR using primers that hybridize to a sequence in the adaptor, or complement thereof), and then sequenced to produce a plurality of sequence reads. After sequencing, the method may comprise assembling any overlapping sequence reads, thereby obtaining a contig containing the sequence of at least part of the first sequence of interest and at least part of the second sequence of interest.

As would be apparent, the adaptors and/or the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. Indeed, if the products are amplified on a solid support (e.g., using an Illumina flow cell), then the amplicons may be sequenced in place on the substrate. The sequencing step may be done using any convenient next generation sequencing method and may result in at least 10,000, at least 50,000, at least 100,000, at least 500,000, at least 1M at least 10M at least 100M or at least 1B sequence reads. In many cases, the reads are paired-end reads.

In any embodiment, prior to digestion, the method may comprise end-blocking the mixed nucleic acid sample so that the ends of the nucleic acid fragments are not available for ligation. For example, in any embodiment described above, prior to digestion, the method may comprise treating the mixed nucleic acid sample with a phosphatase (e.g., CIP, SAP, PLAP or SEAP) thereby removing the 5' phosphate groups from the nucleic acid in the sample and making the 5' ends of the nucleic acid in the sample unligatable. Alternative blocking methods are also possible, including ligation of a hairpin adaptor, ligation of an adaptor containing a chemical blocking group, ligation of an adaptor lacking a 5 prime phosphate, chemical addition of a blocking group, enzyme-mediated addition of a modified nucleotide, enzyme-mediated addition of one or more nucleotides producing a sticky end overhang that is incompatible with the future ligation of the a specific adaptor, or any other method that prevents efficient downstream ligation of a functional adaptor.

In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

Figure 4:
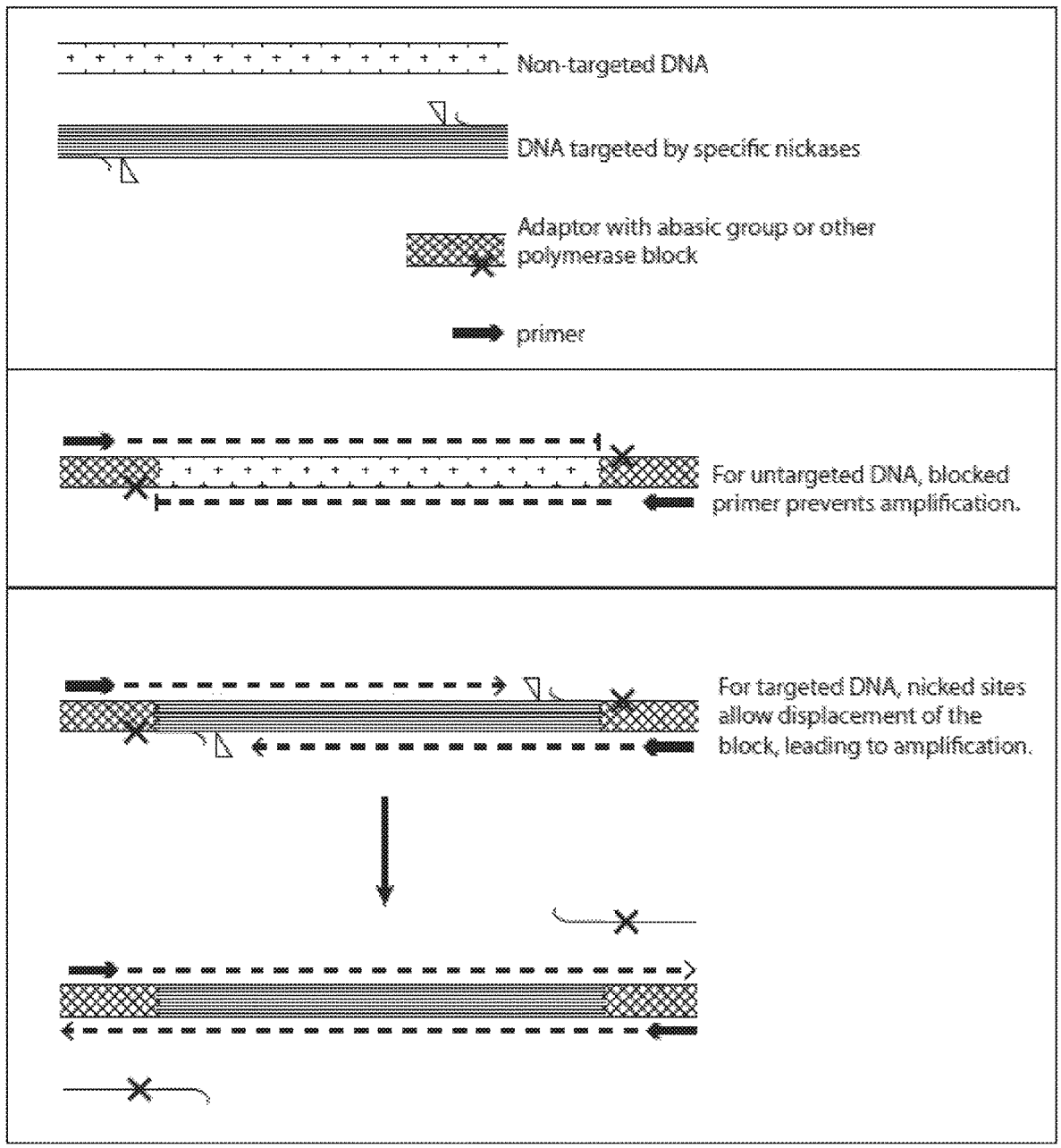
FIG. 4 depicts an alternative version of the method in which blocked adapters are ligated to fragmented DNA, preventing amplification by polymerase unless targeted nickases (such as Cas9 with a single active site mutation, D10A) make single-stranded cuts that allow displacement of the blocked strand of the adaptor. The result is that only inserts containing two nickase sites is amplified.

In some embodiments, DNA samples can be ligated with blocked adapters to prevent amplification. Prior to amplification, ligated samples can be treated with a targeted nickase, such as Cas9 D10A. Nicking will allow extension of the targeted sequences and displacement of the blocking groups only in the adapters attached to those sequences, allowing PCR amplification of nicked molecules while non-targeted molecules cannot be amplified. Examples of blocking groups include, but are not limited to, deoxyuracil (dU), inverted deoxythymidine (dT), RNA bases, deoxyisocytidine (isodC), deoxyisoguanine (isodG), 1',2'-dideoxynucleotides (ddNTPs), spacers, abasic sites, and others. This embodiment of the method is depicted in FIG. 4. This method may comprise ligating adaptors to the ends of the fragments, where the adaptors contain a blocking group (i.e., a group that causes polymerases to stall), nicking the target fragments using a nucleic acid-guided nicking endonuclease (e.g., Cas9 D10A), extending the nicked strands to displace the strand that contains the blocking group, and then amplifying the target sequences using generic primers that hybridize to the adaptors.

In some embodiments, the nucleic acid sample may comprise DNA from at least two organisms, e.g., a mammal and a pathogen (where the pathogen may be a virus, bacteria or fungus, for example), a mammal and a microbiome, or two microorganisms in a microbiome, where the DNA from one of the organisms may be at least 10 times, at least 50 times, or at least 100 times, at least 500 times or at least 1,000 times more abundant than the other. In some embodiments, the nucleic acid sample may contain wild type and mutant DNA from the same organism (e.g., a cancer patient). In some embodiments, the mixed sample may be an environmental sample, a sample from a crime scene or an archaeological sample. In some embodiments, the mixed sample is made from a clinical sample, e.g., from a patient suspected of having been infected by a pathogen. The clinical sample may a bodily fluid or excretion listed below. In some embodiments, the clinical sample may be a tumor biopsy. Methods for extracting total DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit and urine. In particular embodiments, the sample may be a clinical sample, e.g., a sample collected from a patient. In certain cases, the DNA in these samples may be highly fragmented, e.g., to an average size in the range of 10 bp to 5 kb, e.g., 20 bp to 200 bp and in certain cases may be fragmented using the methods described herein. Methods for extracting total DNA from such samples are well known.

The above described method is useful for the analysis of samples in a variety of diagnostic, drug discovery, and research applications. The above described method is useful for the analysis of biological samples. The term "biological sample," as used herein, refers to a sample obtained from an organism or from components (e.g., cells) of an organism. The sample may be of any biological tissue or fluid. In some cases, the sample will be a "clinical sample" which is a sample derived from a patient. Such samples include, but are not limited to, sputum, blood, blood cells (e.g., white blood cells), tissue or fine needle biopsy samples, urine, peritoneal fluid, and pleural fluid, or cells there from. Biological samples may also include sections of tissues such as frozen sections taken for histological purposes. The subject method also finds use in determining the identity of microbes in water, sewage, air samples, food products, including animals, vegetables, seeds, etc., soil samples, plant samples, microbial culture samples, cell culture samples, tissue culture samples, as well as in human medicine, veterinary medicine, agriculture, food science, bioterrorism, and industrial microbiology, etc. The subject method allows identification of hard to culture microbes since culturing the microbes is not necessary. Consequently, the subject method provides for a rapid detection of microbes in a sample with no waiting period for culturing microbes.

In some embodiments, the method may be employed to identify a microbial pathogen from a clinical sample. In these embodiments, the endonucleases may target sequences from multiple different pathogens (e.g., at least 10 or at least 100 different pathogens), without knowing which pathogen is responsible for an infection, the enriched nucleic acid may be sequenced, and the sequences may be compared to sequences from known pathogens, e.g., bacterial, east and viral pathogens, and, if a match is found, then the subject may be diagnosed as being infected by that pathogen. In some embodiments, the nuclease may be programmed with a degenerate recognition sequence representing a known conserved motif coding for a particular gene or genes involved in a molecular pathway of interest. In this way, homologous genes from several species may be enriched for and sequenced simultaneously. In another embodiment, the method may be used for deep sequencing of a host-associated communities (a "microbiome"), with the advantage that the method enables sequencing of all microbial DNA in the sample, not only a subset of the DNA e.g., ribosomal DNA only. Microbes that might be identified using the present methods, compositions and kits include but are not limited to: a plurality of species of Gram (+) bacteria, plurality of species of Gram (−) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*, *Escherichia coli* (*E. coli*), *E. coli* of various strains such as, K12-MG1655, CFT073, O157:H7 EDL933, O157:H7 VT2-Sakai, etc., *Streptococcus pneumoniae*, *Pseudomonas aeruginosa*, *Staphylococcus aureus*, coagulase-negative staphylococci, a plurality of *Candida* species including *C. albicans, C. tropicalis, C. dubliniensis, C. viswanathii, C. parapsilosis, Klebsiella pneumoniae*, a plurality of *Mycobacterium* species such as *M. tuberculosis, M. bovis, M. bovis* BCG, *M. scrofulaceum, M. kansasii, M. chelonae, M. gordonae, M. ulcerans, M. genavense, M. xenoi, M. simiae, M. fortuitum, M. malmoense, M. celatum, M. haemophilum* and *M. africanum*, *Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

Disease states may exhibit either the presence of a novel microbe(s), absence of a normal microbe(s), or an alteration in the proportion of microbes. Disease states may also have substantially similar microbial populations as normal states, but with a different microbial function or a different host response to the microbes due to environmental or host genetic factors. For example, recent research has established that disruption of the normal equilibrium between a host and its microbiota, generally manifested as a microbial imbalance, is associated with, and may lead to, a number of conditions and diseases. These include Crohn's disease, ulcerative colitis, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions such as autism spectrum disorders, and numerous infections, among others. For example, in Crohn's disease, concentrations of Bacterioides, Eubacteria and *Peptostreptococcus* are increased whereas Bifidobacteria numbers are reduced (Linskens et al., Scand J Gastroenterol Suppl. 2001; (234):29-40); in ulcerative colitis, the number of facultative anaerobes is increased. In these inflammatory bowel diseases, such microbial imbalances cause increased immune stimulation, and enhanced mucosal permeability (Sartor, Proc Natl Acad Sci USA. 2008 Oct. 28; 105(43):16413-4). In obese subjects, the relative proportion of Bacteroidetes has been shown to be decreased relative to lean people (Ley et al., Nature. 2006 Dec. 21; 444(7122):1022-3), and possible links of microbial imbalances with the development of diabetes have also been discussed (Cani et al., Pathol Biol (Paris). 2008 July; 56(5):305-9). In the skin, a role for the indigenous microbiota in health and disease has been suggested in both infectious and noninfectious diseases and disorders, such as atopic dermatitis, eczema, rosacea, psoriasis, and acne (Holland et al. Br. J. Dermatol. 96:623-626; Thomsen et al. Arch. Dermatol. 116:1031-1034; Till et al. Br. J. Dermatol. 142:885-892; Paulino et al. J. Clin. Microbiol. 44:2933-2941). Furthermore, the resident microbiota may also become pathogenic in response to an impaired skin barrier (Roth and James Annu Rev Microbiol. 1988; 42:441-64). Bacterial vaginosis is caused by an imbalance of the naturally occurring vaginal microbiota. While the normal vaginal microbiota is dominated by *Lactobacillus*, in grade 2 (intermediate) bacterial vaginosis, *Gardnerella* and *Mobiluncus* spp. are also present, in addition to Lactobacilli. In grade 3 (bacterial vaginosis), *Gardnerella* and *Mobiluncus* spp. predominate, and Lactobacilli are few or absent (Hay et al., Br. Med. J., 308, 295-298, 1994). Identification of which microbes are in a sample may aid in the diagnosis and treatment of such diseases.

In addition, the method may be used to detect an RNA virus or a reverse transcribing virus, e.g., reovirus, rotavirus, enterovirus, rhinovirus, hepatovirus, cardiovirus, aphthovirus, poliovirus, parechovirus, erbovirus, kobuvirus, teschovirus, coxsackie, norwalk virus, rubella virus, alphavirus, lymphocytic choriomeningitis virus, dengue virus, hepatitis C virus, yellow fever virus, influenzavirus A, influenzavirus B, influenzavirus C, isavirus, thogotovirus, measles virus, mumps virus, respiratory syncytial virus, Rinderpest virus, canine distemper virus, California encephalitis virus, hantavirus, rabies virus, Ebola virus, Marburg virus, corona virus, astrovirus, borna disease virus, arterivirus, equine arteritis virus, hepatitis E virus, retroviruses (e.g., HIV-1 and HIV-2) and hepatitis B virus.

The method may also be used to detect microbial DNA or RNA sequences and simultaneously detect human DNA or RNA sequences, allowing the study of pathogen and host in the same experiment.

The method may also be used for genotyping. In this case it would target particular sites within a pathogen or other species that can be used to differentiate specific strains or other subpopulations. In the case of infection with multiple subpopulations, or detection of multiple subpopulations in a microbiome or environmental sample, this method, applied either with or without unique molecular identifiers (UMIs) can be used to assess relative amounts of the different subpopulations.

In some embodiments, the method can be used to determine the target sequence of nucleases such as restriction endonucleases, homing endonucleases, and programmable nucleases such as Cas9 or Cpf1. For example, to identify cleavage sites of a particular Cas9 guide RNA combination, a genomic DNA library synthesized with blocked adapters can be treated with the Cas9 and guideRNA to allow selective amplification of sequences containing cleavage sites.

These and other uses of the method would be readily apparent.

Kits

Also provided by the present disclosure are kits for practicing the present method as described above. In certain embodiments, a subject kit may contain: a) a plurality of reprogrammed nucleic acid-directed endonucleases; and b) a phosphatase or other blocking reagent. Such a kit may optionally contain an adaptor and PCR primers, wherein the 3' end of the PCR primers has a sequence that is the same as or complementary to a sequence in the adaptors. Further details of the components of this kit are described above. The kit may also contain other reagents described above and below that may be employed in the method, e.g., a ligase, polymerase, etc., depending on how the method is going to be implemented.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In order to further illustrate the present invention, the following specific examples are given with the understanding that they are being offered to illustrate the present invention and should not be construed in any way as limiting its scope.

EMBODIMENTS

Embodiment 1A

A method of sample analysis, comprising: (a) digesting an end-blocked mixed nucleic acid sample with a plurality of reprogrammed nucleic acid-directed endonucleases that target sequences of interest to produce a digested sample, wherein at least some of the fragments in the digested sample comprise: (i) a sequence of interest and (ii) at least one ligatable end that has been generated by endonuclease cleavage; (b) enriching for fragments that contain the sequence of interest; and (c) analyzing the enriched fragments.

Embodiment 1B

A method of sample analysis, comprising:
(a) digesting a phosphatase-treated mixed nucleic acid sample with a plurality of reprogrammed nucleic acid-directed endonucleases that target sequences of interest to produce a digested sample, wherein at least some of the fragments in the digested sample comprise: (i) a sequence of interest and (ii) at least one ligatable end that has been generated by endonuclease cleavage; (b) enriching for fragments that contain the sequence of interest; and (c) analyzing the enriched fragments.

Embodiment 2

The method of embodiment 1A or B, wherein the method comprises ligating an adaptor to the ligatable ends generated by endonuclease cleavage in step (a).

Embodiment 3

The method of embodiment 2, wherein the adaptor comprises capture moiety and the enriching is done by binding the capture moiety to a support, and washing away the unbound nucleic acid.

Embodiment 4

The method of any prior embodiment, wherein the endonucleases digestion of (a) produces fragments of in a defined size range.

Embodiment 5

The method of embodiment 4, wherein the enriching is done by size selecting the fragments.

Embodiment 6

The method of any prior embodiment, wherein the endonuclease digestion of (a) produces fragments that have ends that are both ligatable.

Embodiment 7

The method of any prior embodiment, wherein digestion of (a) creates fragments that ligatable endonuclease cleavage sites on both ends, and the method comprises ligating adaptors to both ends of the fragments.

Embodiment 8

The method of embodiment 7, wherein the enriching is done by amplifying the ligated fragments using primers that hybridize to the adaptors, or complements thereof.

Embodiment 9

The method of embodiment 8, wherein the adaptors contain a molecule indexer.

Embodiment 10

The method of any prior embodiment, wherein the method comprises ligating indexed adaptors to both ends of the fragments where the index is a series of random nucleotides long enough that there is a high probability of every fragment receiving a distinct index, sequencing the ligated fragments to produce sequence reads, and then counting the number of molecule indexer sequences that are associated with a sequence of interest in the sequence reads, thereby provide an estimate of the copy number of the sequence of interest in the nucleic acid sample.

Embodiment 11

The method of any prior embodiment, wherein the method comprises:
(a) separately digesting:
(I) a first portion of the mixed nucleic acid sample with a plurality of reprogrammed nucleic acid-directed endonucleases that target sequences of interest to produce a first digested sample, wherein at least some of the fragments in the digested sample comprise: (i) a first sequence of interest and (ii) at least one ligatable end that has been generated by endonuclease cleavage;
(II) a second portion of the mixed nucleic acid sample with a plurality of reprogrammed nucleic acid-directed endonucleases that target sequences of interest to produce a second digested sample, wherein at least some of the fragments in the digested sample comprise: (i) a second sequence of interest and (ii) at least one ligatable end that has been generated by endonuclease cleavage;
wherein at least some of the fragments in the first digested sample overlap with at least some of the fragments in the second digested sample;
(b) enriching for fragments that contain the sequences of interest;
(c) sequencing the enriched sequences to produce a plurality of sequence reads; and
(d) assembling overlapping sequence reads, thereby obtaining a contig of a first sequence of interest and a second sequence of interest.

Embodiment 12

The method of any prior embodiment, wherein the ligatable ends generated by endonuclease treatment are blunt ends.

Embodiment 13

The method of any prior embodiment, wherein the mixed nucleic acid sample comprises DNA from at least two organisms.

Embodiment 14

The method of embodiment 13, wherein the at least two organisms comprise a mammal and a pathogen.

Embodiment 15

The method of embodiment 14, wherein the pathogen is a virus, bacteria or fungus Embodiment 16

The method of embodiment 15, wherein the at least two organisms comprise a mammal and a microbiome.

Embodiment 17

The method of any prior embodiment, wherein the wherein the mixed sample comprises wild type and mutant DNA.

Embodiment 18

The method of any prior embodiment, wherein the mixed sample is an environmental sample, a sample from a crime scene or an archaeological sample.

Embodiment 19

The method of any prior embodiment, wherein the mixed sample is made from a clinical sample.

Embodiment 20

The method of embodiment 19, wherein the clinical sample is a bodily fluid or excretion.

Embodiment 21

The method of embodiment 20, wherein the clinical sample is blood, sputum, or feces.

Embodiment 22

The method of embodiment 20, wherein the clinical sample is a tumor biopsy.

Embodiment 23

The method of any prior embodiment, wherein the analyzing of (c) is done by sequencing.

Embodiment 24

The method of any prior embodiment, wherein the endonuclease is cas9 or Argonaught, an ortholog thereof, or a variant thereof.

Embodiment 25

The method of any prior embodiment, wherein the sample is digested by at least 2 reprogrammed nucleic acid-directed endonucleases.

Embodiment 26

The method of any prior embodiment, wherein, prior to step (a), the method comprises treating the mixed nucleic acid sample with a phosphatase, thereby making the 5' ends of the nucleic acid in the sample unligatable.

Embodiment 27A

A kit comprising a plurality of reprogrammed nucleic acid-directed endonucleases; and a phosphatase.

Embodiment 27B

A kit comprising a plurality of reprogrammed nucleic acid-directed endonucleases; and a phosphatase or other end-blocking reagent.

Embodiment 28

The kit of embodiment 27A or B, further comprising an adaptor.

Embodiment 29

The kit of embodiment 27A or B, further comprising PCR primers, wherein the 3' end of the PCR primers has a sequence that is the same as or complementary to a sequence in the adaptors.

EXAMPLES

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Using FLASH to target antibiotic resistance genes, it was demonstrated that enrichment of sequences such as mecA by over ten fold relative to randomly fragmented cDNA libraries derived from patient samples.

Design and Construction of the Cas9-DGRNA Complex

Thirteen genes capable of conferring antibiotic resistance in *Staph aureus* were chosen for FLASHing in this study. Nine (mecA, Qnr, qacB, MFS, mdeA, NorA, NorB/C, KCTC, and PAO1) are plasmid-borne genes whose presence alone would indicate resistance; the other four (gyrase A, gyrase B, parC and parE) are genes endogenous to *S. aureus* in which specific point mutations are known to cause quinolone resistance. For the plasmid-borne genes, guide RNA sites were chosen near both ends of the genes and approximately every 200-300 bp apart within the genes. For genes with point mutations, two sites were chosen flanking each mutation at a distance that would yield a cleavage product of 200-300 bp. A list of guide RNAs and their positions within the genes can be found in Table 1 below.

TABLE 1

| Gene | Position | crRNA sequence |
|---|---|---|
| GyrA | 111 | CAAAACAGCATAGCTCTAAAACGATGTTCGTGACGGTTTAAACTATAGTGAGTCGTATTA (SEQ ID NO: 1) |
| GyrA | 334 | CAAAACAGCATAGCTCTAAAACTTGAACCAAAGTTACCTTGGCTATAGTGAGTCGTATTA (SEQ ID NO: 2) |
| GyrB | 1132 | CAAAACAGCATAGCTCTAAAACCAAGTCGCACGTACAGTGGTCTATAGTGAGTCGTATTA (SEQ ID NO: 3) |

TABLE 1-continued

| Gene | Position | crRNA sequence |
|---|---|---|
| GyrB | 1451 | CAAAACAGCATAGCTCTAAAACAATGCTGTGATCATTTGACGCTATAGTGAGTCGTATTA (SEQ ID NO: 4) |
| GyrB | 1837 | CAAAACAGCATAGCTCTAAAACCTTCAATCGCATCTTCAAGTCTATAGTGAGTCGTATTA (SEQ ID NO: 5) |
| GyrB | 248 | CAAAACAGCATAGCTCTAAAACCGTCCGTTATCCGTTACTTTCTATAGTGAGTCGTATTA (SEQ ID NO: 6) |
| GyrB | 45 | CAAAACAGCATAGCTCTAAAACAGCACCATAATTATCCGTGTCTATAGTGAGTCGTATTA (SEQ ID NO: 7) |
| GyrB | 536 | CAAAACAGCATAGCTCTAAAACTCTGCTTTAAAACGAATGACCTATAGTGAGTCGTATTA (SEQ ID NO: 8) |
| GyrB | 917 | CAAAACAGCATAGCTCTAAAACTAACTATTTAAGACACGCGTCTATAGTGAGTCGTATTA (SEQ ID NO: 9) |
| KCTC | 1129 | CAAAACAGCATAGCTCTAAAACCAAGAATATGATACGCCGCCCTATAGTGAGTCGTATTA (SEQ ID NO: 10) |
| KCTC | 19 | CAAAACAGCATAGCTCTAAAACTTACAGGCGTACTGCTGCTGCTATAGTGAGTCGTATTA (SEQ ID NO: 11) |
| KCTC | 327 | CAAAACAGCATAGCTCTAAAACGCGCAGAAGTACTGGCCGCACTATAGTGAGTCGTATTA (SEQ ID NO: 12) |
| KCTC | 521 | CAAAACAGCATAGCTCTAAAACATGCTGGCATTGGCGTACAGCTATAGTGAGTCGTATTA (SEQ ID NO: 13) |
| KCTC | 807 | CAAAACAGCATAGCTCTAAAACCTGCCGCAGATTTTATCCTCTATAGTGAGTCGTATTA (SEQ ID NO: 14) |
| mdeA | 1343 | CAAAACAGCATAGCTCTAAAACGCGTGATAACCATGCAACATCTATAGTGAGTCGTATTA (SEQ ID NO: 15) |
| mdeA | 381 | CAAAACAGCATAGCTCTAAAACACCACATGAACGCGGTAAATCTATAGTGAGTCGTATTA (SEQ ID NO: 16) |
| mdeA | 44 | CAAAACAGCATAGCTCTAAAACCCCATCAGCATAGTAATAATCTATAGTGAGTCGTATTA (SEQ ID NO: 17) |
| mdeA | 629 | CAAAACAGCATAGCTCTAAAACTACAATAACCCGCCGAAACCCTATAGTGAGTCGTATTA (SEQ ID NO: 18) |
| mdeA | 989 | CAAAACAGCATAGCTCTAAAACACTAAAGCAAGATTTCTAGGCTATAGTGAGTCGTATTA (SEQ ID NO: 19) |
| mecA | 1156 | CAAAACAGCATAGCTCTAAAACAAGATAAAAAAGAACCTCTGCTATAGTGAGTCGTATTA (SEQ ID NO: 20) |
| mecA | 1418 | CAAAACAGCATAGCTCTAAAACAATTCGAGTGCTACTCTAGCCTATAGTGAGTCGTATTA (SEQ ID NO: 21) |
| mecA | 1668 | CAAAACAGCATAGCTCTAAAACAACTTTGTTTTTCGTGTCTTCTATAGTGAGTCGTATTA (SEQ ID NO: 22) |
| mecA | 1882 | CAAAACAGCATAGCTCTAAAACTCATCATGTTTGGATTATCTCTATAGTGAGTCGTATTA (SEQ ID NO: 23) |
| mecA | 2090 | CAAAACAGCATAGCTCTAAAACTTAAATACAATTTCTTCATTCTATAGTGAGTCGTATTA (SEQ ID NO: 24) |
| mecA | 215 | CAAAACAGCATAGCTCTAAAACAAACTATTATATATTTTATCTATAGTGAGTCGTATTA (SEQ ID NO: 25) |
| mecA | 28 | CAAAACAGCATAGCTCTAAAACCTTATTTTAATAGTTGTAGTCTATAGTGAGTCGTATTA (SEQ ID NO: 26) |
| mecA | 475 | CAAAACAGCATAGCTCTAAAACCATTGTTTCGGTCTAAAATTCTATAGTGAGTCGTATTA (SEQ ID NO: 27) |
| mecA | 735 | CAAAACAGCATAGCTCTAAAACCTAGAAAAGCGACTTCACACTATAGTGAGTCGTATTA (SEQ ID NO: 28) |
| mecA | 95 | CAAAACAGCATAGCTCTAAAACTCTTTTTTCTTTTTCTCTATCTATAGTGAGTCGTATTA (SEQ ID NO: 29) |

TABLE 1-continued

| Gene | Position | crRNA sequence |
|---|---|---|
| MFS | 1294 | CAAAACAGCATAGCTCTAAAACTTGCGATGTACTTTCATTGACTATAGTGAGTCGTATTA (SEQ ID NO: 30) |
| MFS | 305 | CAAAACAGCATAGCTCTAAAACGTAGTATTTATCGGCATCATCTATAGTGAGTCGTATTA (SEQ ID NO: 31) |
| MFS | 588 | CAAAACAGCATAGCTCTAAAACGCGCTGCTTATACCGCTATACTATAGTGAGTCGTATTA (SEQ ID NO: 32) |
| MFS | 75 | CAAAACAGCATAGCTCTAAAACTAACAAGCACAGCTACAAAACTATAGTGAGTCGTATTA (SEQ ID NO: 33) |
| MFS | 894 | CAAAACAGCATAGCTCTAAAACAACCGAAAACAAAGGCAAGTCTATAGTGAGTCGTATTA (SEQ ID NO: 34) |
| NorA | 1100 | CAAAACAGCATAGCTCTAAAACGCTAATGAAACACCTATAGCCTATAGTGAGTCGTATTA (SEQ ID NO: 35) |
| NorA | 410 | CAAAACAGCATAGCTCTAAAACGAATTGATAATCGCTGACATCTATAGTGAGTCGTATTA (SEQ ID NO: 36) |
| NorA | 748 | CAAAACAGCATAGCTCTAAAACCAAATATACCGCCACCCGTACTATAGTGAGTCGTATTA (SEQ ID NO: 37) |
| NorA | 76 | CAAAACAGCATAGCTCTAAAACGTCTTGCCTGTTTATTTAAACTATAGTGAGTCGTATTA (SEQ ID NO: 38) |
| NorB/C | 1360 | CAAAACAGCATAGCTCTAAAACAATGATGATAAACGTGTCAACTATAGTGAGTCGTATTA (SEQ ID NO: 39) |
| NorB/C | 17 | CAAAACAGCATAGCTCTAAAACCCGCGATACGTTTCATTCATCTATAGTGAGTCGTATTA (SEQ ID NO: 40) |
| NorB/C | 355 | CAAAACAGCATAGCTCTAAAACTCCACATTGGCCATTATGAACTATAGTGAGTCGTATTA (SEQ ID NO: 41) |
| NorB/C | 650 | CAAAACAGCATAGCTCTAAAACTTAGTAATGACAACGTTTAACTATAGTGAGTCGTATTA (SEQ ID NO: 42) |
| NorB/C | 995 | CAAAACAGCATAGCTCTAAAACAATAACATTGGTCGCTTAGACTATAGTGAGTCGTATTA (SEQ ID NO: 43) |
| PAO1 | 1166 | CAAAACAGCATAGCTCTAAAACTGCTGCTCCAGGCCGCTGAGCTATAGTGAGTCGTATTA (SEQ ID NO: 44) |
| PAO1 | 16 | CAAAACAGCATAGCTCTAAAACGATTCCCCTGCCTGTGCGGCCTATAGTGAGTCGTATTA (SEQ ID NO: 45) |
| PAO1 | 260 | CAAAACAGCATAGCTCTAAAACATCTCGAACAGGGTCTCCGGCTATAGTGAGTCGTATTA (SEQ ID NO: 46) |
| PAO1 | 489 | CAAAACAGCATAGCTCTAAAACCTGGCGGTAGTAGTCGCGGACTATAGTGAGTCGTATTA (SEQ ID NO: 47) |
| PAO1 | 708 | CAAAACAGCATAGCTCTAAAACTAGCGGGCGGTCGTCCTTGCCTATAGTGAGTCGTATTA (SEQ ID NO: 48) |
| PAO1 | 954 | CAAAACAGCATAGCTCTAAAACATGGCGCTGCAACCGCACAGCTATAGTGAGTCGTATTA (SEQ ID NO: 49) |
| parC | 123 | CAAAACAGCATAGCTCTAAAACGTACAACGTCGTATTTTATACTATAGTGAGTCGTATTA (SEQ ID NO: 50) |
| parC | 342 | CAAAACAGCATAGCTCTAAAACCCAGCTGCAATGCGTTACACCTATAGTGAGTCGTATTA (SEQ ID NO: 51) |
| parE | 1158 | CAAAACAGCATAGCTCTAAAACTGCTTGTTGTGCTTTAATCGCTATAGTGAGTCGTATTA (SEQ ID NO: 52) |
| parE | 1448 | CAAAACAGCATAGCTCTAAAACGCCCCGATTGTGTGGATAATCTATAGTGAGTCGTATTA (SEQ ID NO: 53) |
| qacB | 1007 | CAAAACAGCATAGCTCTAAAACAATCGCGCCGCTAATCCGGGCTATAGTGAGTCGTATTA (SEQ ID NO: 54) |
| qacB | 1232 | CAAAACAGCATAGCTCTAAAACAGGTCATACATAGACTCTTCCTATAGTGAGTCGTATTA (SEQ ID NO: 55) |

TABLE 1-continued

| Gene | Position | crRNA sequence |
|---|---|---|
| qacB | 1464 | CAAAACAGCATAGCTCTAAAACACCTACTAAAGCAGTTGCTACTATAGTGAGTCGTATTA (SEQ ID NO: 56) |
| qacB | 152 | CAAAACAGCATAGCTCTAAAACGAAGGCTCTAACTCTCTTACCTATAGTGAGTCGTATTA (SEQ ID NO: 57) |
| qacB | 356 | CAAAACAGCATAGCTCTAAAACGCAATACCAAGTAAAAATCGCTATAGTGAGTCGTATTA (SEQ ID NO: 58) |
| qacB | 618 | CAAAACAGCATAGCTCTAAAACCGAGTGAGACTTTTCTTTTGCTATAGTGAGTCGTATTA (SEQ ID NO: 59) |
| Qnr | 241 | CAAAACAGCATAGCTCTAAAACAGCGCGCTCACATTCCTGAACTATAGTGAGTCGTATTA (SEQ ID NO: 60) |
| Qnr | 346 | CAAAACAGCATAGCTCTAAAACGTACCTGAGTACCCATCCAACTATAGTGAGTCGTATTA (SEQ ID NO: 61) |
| Qnr | 44 | CAAAACAGCATAGCTCTAAAACGTGAATCTGTTTCTGTCAATCTATAGTGAGTCGTATTA (SEQ ID NO: 62) |
| Qnr | 635 | CAAAACAGCATAGCTCTAAAACATGACAGCGATGCCAAGACGCTATAGTGAGTCGTATTA (SEQ ID NO: 63) |

Dual guide RNAs were chosen instead of single guide RNAs because of the reduced cost. For each chosen target, a 60mer crRNA template oligo was designed including the 18-base T7 transcription start site, the targeted 20mer, and the remaining 22 bases of the crRNA; the reverse complement of this sequence was purchased (5'-CAAAACAGCAT-AGCTCTAAAACNNNNNNNNNNNNNNNNNNNNCT-ATAGTGAGTCG TATTA-3') (SEQ ID NO: 64). All oligos were purchased from IDT (Integrated DNA Technologies, Coralville, Iowa, USA). All crRNAs were pooled for transcription. Transcription was performed using custom-made T7 RNA polymerase (RNAP). In each 100 µL reaction, 400 ng of DNA template was mixed with T7 RNAP (final concentration 8 ng/µL), buffer (final concentrations of 40 mM Tris pH 8.0, 20 mM MgCl2, 5 mM DTT, and 2 mM spermidine), and NTPs (ThermoFisher Scientific, Waltham, Mass., USA) (final concentration 1 mM each ATP, CTP, GTP and UTP), and incubated at 37° C. for 4 hours. Typical yields were 10 to 50 µg of RNA. crRNAs were purified with a Zymo RNA Clean & Concentrator-5 kit (Zymo Research, Irvine, Calif., USA).

Synthetic tracrRNA was obtained from IDT. The crRNA library was complexed with tracrRNA by mixing the two components at equimolar concentrations, heating the mixture at 95 degrees for 1 minute, and then slowly cooling it to room temperature on the benchtop. The resulting dgRNA was aliquoted, stored at −80° C., and used only a single time after thawing.

Cas9 tagged with mRuby2 was expressed and purified as described in Gu & Crawford et al. 2016 [1].

Flashing and Deep Sequencing Culture and Patient Samples

Genomic DNA was prepared from patient culture isolates (samples 31 and 33) using standard procedures. cDNA was prepared from patient bronchoalveolar lavage (BAL) fluid (samples 288 and 1002) using the NuGEN Ovation v.2 kit (NuGEN, San Carlos, Calif., USA) for low nucleic acid content samples, as described in [2,3]. Ten nanograms of DNA from each sample was treated with calf intestinal phosphatase (CIP) for 30 minutes at 37° C. in order to dephosphorylate all 5' DNA ends present. Samples were spin-column purified to remove the CIP. The RNP complex was formed by mixing the RNA library with Cas9 at a concentration of 40 uM each in 1×Cas9 activity buffer (final concentrations of 50 mM Tris pH 8.0, 100 mM NaCl, 10 mM MgCl2, and 1 mM TCEP) and incubating at 37° C. for 10 minutes. The Cas9-guide RNA complex was then added to the CIP-treated DNA at a final concentration of 10 uM RNP in a total volume of 20 µL with 1×Cas9 activity buffer. After a 2 hour incubation at 37° C., samples were treated with proteinase K for 15 minutes at 37° C. and then boiled at 95 for 5 minutes. Samples were then cleaned up with ampure beads at a ratio of 1:1.4. They were eluted in 20 µL of water.

As a control, an additional 10 ng of each DNA sample was treated with NEBNext Fragmentase enzyme for 25 minutes, according to manufacturer's instructions.

Cas9-cleaved DNA and fragmentase-cleaved DNA samples were converted into Illumina sequencing libraries using the NEBNext Ultra II library preparation kit according to manufacturer's instructions, and amplified with dual-index barcode primers.

Amplified samples were purified with ampure beads at a ratio of 1:0.9 and then quantified by Qubit and pooled at equal concentrations. A Bioanalyzer high-sensitivity DNA kit trace showed a large peak at approximately 140 bp, indicating adaptor dimers. Samples were therefore re-purified with ampure beads at a ratio of 1:0.8 and amplified with 6 more cycles of PCR using the KAPA library amplification kit and Illumina universal P5 and P7 primers. A repeated Bioanalyzer trace showed that the peak at 140 bp had been removed and a broad peak centered around 200-300 bp remained. Libraries were quantified by ddPCR (Bio-Rad, Hercules, Calif., USA). Sequencing was performed on portions of two lanes in an Illumina HiSeq 2500 instrument using 125 bp paired-end sequencing.

Data was filtered using PriceSeqFilter [4] and then run through an in-house pathogen discovery pipeline (as described in Gu & Crawford et al 2016 [1]).

Results

Figure 3:
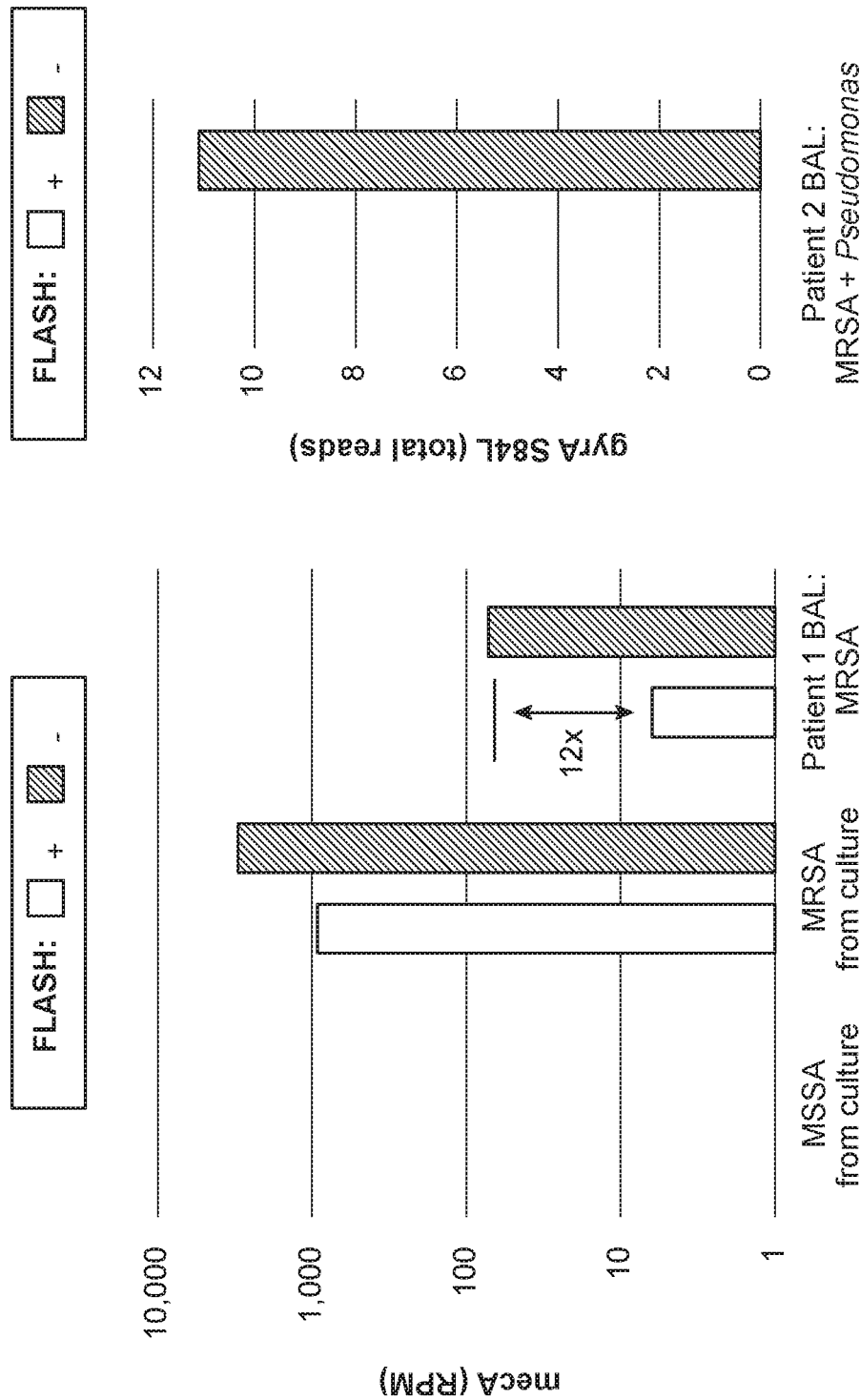
FIG. 3 panel A shows the abundance of mecA from i) cultured isolates of methicillin-sensitive Staphylcoccus areaus (MSSA), ii) methicillin-resistant Stepylococcus aureas (MRSA) and iii) direct BAL fluid from patient with MRSA pneumonia. Detectable mecA in BAL fluid from patient with MRSA pneumonia is increased with FLASH. Panel B shows that FLASH permits detection of fluoroquinolone resistance mutation GyrA S84L in BAL fluid from patent with MRSA and *Pseudomonas aeruginosa* pneumonia.

FIG. 3 depicts enrichment of the targeted antibiotic resistance genes with FLASH. In the absence of FLASH, mecA is readily detectable in culture isolates but difficult to detect in cDNA prepared from patient samples. FLASH increases mecA coverage by 12 fold.

Discussion

The FLASH method is not limited to the protocol described here. In other instances, rather than adaptor ligation, the liberated section of DNA could be isolated by size selection, and then amplified or ligated after isolation. In cases where only one cleavable sequence in a particular gene of interest is known, sequence-specific nuclease digestion can be followed by ligation of a chemically labeled oligonucleotide attached to a label (such as biotin) for the purpose of capturing and purifying the desired sequence. Random fragmentation followed by another adaptor ligation step can then be used to purify and amplify the DNA molecule containing the original sequence.

To add a quantitative aspect to this technique, adaptors can include UMI (unique molecular identifier) sequences. UMIs are degenerate sequences (e.g. NNNNNNNNNNNN) placed adjacent to the barcodes on the adaptors or on indexing primers. If placed on indexing primers, in the very first cycle of the indexing PCR, each individual molecule in the sample will be amplified with a primer containing the same barcode but a different, unique UMI. In subsequent cycles, the UMI sequence will be amplified. When the library is sequenced, the number of UMIs counted for each sequenced fragment is an indication of the number of copies of that fragment present in the original sample following nuclease treatment.

In addition, guide RNAs could be constructed with degenerate sequences to target conserved regions of sequence in samples that may contain unknown species (or known species whose genomes haven't been sequenced). This would allow, for example, for profiling the metabolic capacities present in a metagenomic sample such as a human microbiome sample.

REFERENCES

1. Gu W, Crawford E D, O'Donovan B D, Wilson M R, Chow E D, Retallack H, et al. Depletion of Abundant Sequences by Hybridization (DASH): using Cas9 to remove unwanted high-abundance species in sequencing libraries and molecular counting applications. Genome Biol. 2016; 17:1-13.
2. Wilson M R, Naccache S N, Samayoa E, Biagtan M, Bashir H, Yu G, et al. Actionable Diagnosis of Neuroleptospirosis by Next-Generation Sequencing. N. Engl. J. Med. 2014; 370:2408-17.
3. Wilson M R, Shanbhag N M, Reid M J, Singhal N S, Gelfand J M, Sample H A, et al. Diagnosing *Balamuthia mandrillaris* Encephalitis With Metagenomic Deep Sequencing. Ann. Neurol. 2015; 78:722-30.
4. Ruby J G, Bellare P, Derisi J L. PRICE: software for the targeted assembly of components of (Meta) genomic sequence data. G3 Bethesda Md. 2013; 3:865-80.

The invention claimed is:

1. A method of sample analysis, comprising:
   (a) digesting a phosphatase-treated mixed nucleic acid sample with a plurality of reprogrammed nucleic acid-directed endonucleases that target sequences of interest to produce a digested sample, wherein at least some of the fragments in the digested sample comprise: (i) a sequence of interest and (ii) at least one ligatable end that has been generated by endonuclease cleavage;
   (b) enriching for fragments that contain the sequence of interest; and
   (c) analyzing the enriched fragments.

2. The method of claim 1, wherein the method comprises ligating an adaptor to the ligatable ends generated by endonuclease cleavage in step (a).

3. The method of claim 2, wherein the adaptor comprises capture moiety and the enriching is done by binding the capture moiety to a support, and washing away the unbound nucleic acid.

4. The method of claim 1, wherein the endonucleases digestion of (a) produces fragments of in a defined size range.

5. The method of claim 4, wherein the enriching is done by size selecting the fragments.

6. The method of claim 1, wherein the endonuclease digestion of (a) produces fragments that have ends that are both ligatable.

7. The method of claim 1, wherein digestion of (a) creates fragments having ligatable endonuclease cleavage sites on both ends, and the method comprises ligating adaptors to both ends of the fragments.

8. The method of claim 7, wherein the enriching is done by amplifying the ligated fragments using primers that hybridize to the adaptors, or complements thereof.

9. The method of claim 8, wherein the adaptors contain a molecule indexer.

10. The method of claim 1, wherein the method comprises ligating indexed adaptors to both ends of the fragments where the index is a series of random nucleotides long enough that there is a high probability of every fragment receiving a distinct index, sequencing the ligated fragments to produce sequence reads, and then counting the number of molecule indexer sequences that are associated with a sequence of interest in the sequence reads, thereby provide an estimate of the copy number of the sequence of interest in the nucleic acid sample.

11. The method of claim 1, wherein the method comprises:
   (a) separately digesting:
      (I) a first portion of the mixed nucleic acid sample with a plurality of reprogrammed nucleic acid-directed endonucleases that target sequences of interest to produce a first digested sample, wherein at least some of the fragments in the digested sample comprise: (i) a first sequence of interest and (ii) at least one ligatable end that has been generated by endonuclease cleavage;
      (II) a second portion of the mixed nucleic acid sample with a plurality of reprogrammed nucleic acid-directed endonucleases that target sequences of interest to produce a second digested sample, wherein at least some of the fragments in the digested sample comprise: (i) a second sequence of interest and (ii) at least one ligatable end that has been generated by endonuclease cleavage;
      wherein at least some of the fragments in the first digested sample overlap with at least some of the fragments in the second digested sample;
   (b) enriching for fragments that contain the sequences of interest;
   (c) sequencing the enriched sequences to produce a plurality of sequence reads; and
   (d) assembling overlapping sequence reads, thereby obtaining a contig of a first sequence of interest and a second sequence of interest.

12. The method of claim 1, wherein the ligatable ends generated by endonuclease treatment are blunt ends.

13. The method of claim 1, wherein the mixed nucleic acid sample comprises DNA from at least two organisms.

14. The method of claim 13, wherein the at least two organisms comprise a mammal and a pathogen.

15. The method of claim 14, wherein the pathogen is a virus, bacteria or fungus.

16. The method of claim 15, wherein the at least two organisms comprise a mammal and a microbiome.

17. The method of claim 1, wherein the wherein the mixed sample comprises wild type and mutant DNA.

18. The method of claim 1, wherein the mixed sample is an environmental sample, a sample from a crime scene or an archaeological sample.

19. The method of claim 1, wherein the mixed sample is made from a clinical sample.

20. The method of claim 19, wherein the clinical sample is a bodily fluid or excretion.

\* \* \* \* \*

SEQUENCE LISTING

```
<160> NUMBER OF SEQ ID NOS: 64

<210> SEQ ID NO 1
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 1
caaaacagca tagctctaaa acgatgttcg tgacggttta aactatagtg agtcgtatta      60

<210> SEQ ID NO 2
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 2
caaaacagca tagctctaaa acttgaacca aagttacctt ggctatagtg agtcgtatta      60

<210> SEQ ID NO 3
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 3
caaaacagca tagctctaaa accaagtcgc acgtacagtg gtctatagtg agtcgtatta      60

<210> SEQ ID NO 4
<211> LENGTH: 60
<212> TYPE: DNA
```

```
<213> ORGANISM: Artificial sequence
<220> FEATURE:
<223> OTHER INFORMATION: synthetic oligonucleotide

<400> SEQUENCE: 4
caaaacagca tagctctaaa acaatgctgt gatcatttga cgctatagtg agtcgtatta      60

<210> SEQ ID NO 5
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 5
caaaacagca tagctctaaa accttcaatc gcatcttcaa gtctatagtg agtcgtatta      60

<210> SEQ ID NO 6
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 6
caaaacagca tagctctaaa accgtccgtt atccgttact ttctatagtg agtcgtatta      60

<210> SEQ ID NO 7
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 7
caaaacagca tagctctaaa acagcaccat aattatccgt gtctatagtg agtcgtatta      60

<210> SEQ ID NO 8
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 8
caaaacagca tagctctaaa actctgcttt aaaacgaatg acctatagtg agtcgtatta      60

<210> SEQ ID NO 9
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 9
caaaacagca tagctctaaa actaactatt taagacacgc gtctatagtg agtcgtatta      60

<210> SEQ ID NO 10
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 10
caaaacagca tagctctaaa accaagaata tgatacgccg ccctatagtg agtcgtatta      60
```

<210> SEQ ID NO 11
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 11
caaaacagca tagctctaaa acttacaggc gtactgctgc tgctatagtg agtcgtatta      60

<210> SEQ ID NO 12
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 12
caaaacagca tagctctaaa acgcgcagaa gtactggccg cactatagtg agtcgtatta      60

<210> SEQ ID NO 13
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 13
caaaacagca tagctctaaa acatgctggc attggcgtac agctatagtg agtcgtatta      60

<210> SEQ ID NO 14
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 14
caaaacagca tagctctaaa acctgccgca gattttatc ctctatagtg agtcgtatta      60

<210> SEQ ID NO 15
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 15
caaaacagca tagctctaaa acgcgtgata accatgcaac atctatagtg agtcgtatta      60

<210> SEQ ID NO 16
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 16
caaaacagca tagctctaaa acaccacatg aacgcggtaa atctatagtg agtcgtatta      60

<210> SEQ ID NO 17
<211> LENGTH: 60
<212> TYPE: DNA
<213> ORGANISM: Artificial sequence
<220> FEATURE:

<223> OTHER INFORMATION: synthetic oligonucleotide

<400> SEQUENCE: 17
caaaacagca tagctctaaa accccatcag catagtaata atctatagtg agtcgtatta        60

<210> SEQ ID NO 18
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 18
caaaacagca tagctctaaa actacaataa cccgccgaaa ccctatagtg agtcgtatta        60

<210> SEQ ID NO 19
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 19
caaaacagca tagctctaaa acactaaagc aagatttcta ggctatagtg agtcgtatta        60

<210> SEQ ID NO 20
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 20
caaaacagca tagctctaaa acaagataaa aaagaacctc tgctatagtg agtcgtatta        60

<210> SEQ ID NO 21
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 21
caaaacagca tagctctaaa acaattcgag tgctactcta gcctatagtg agtcgtatta        60

<210> SEQ ID NO 22
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 22
caaaacagca tagctctaaa acaactttgt ttttcgtgtc ttctatagtg agtcgtatta        60

<210> SEQ ID NO 23
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 23
caaaacagca tagctctaaa actcatcatg tttggattat ctctatagtg agtcgtatta        60

```
<210> SEQ ID NO 24
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 24
caaaacagca tagctctaaa acttaaatac aatttcttca ttctatagtg agtcgtatta       60

<210> SEQ ID NO 25
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 25
caaaacagca tagctctaaa acaaactatt atatatttt atctatagtg agtcgtatta        60

<210> SEQ ID NO 26
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 26
caaaacagca tagctctaaa accttattt aatagttgta gtctatagtg agtcgtatta        60

<210> SEQ ID NO 27
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 27
caaaacagca tagctctaaa accattgttt cggtctaaaa ttctatagtg agtcgtatta       60

<210> SEQ ID NO 28
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 28
caaaacagca tagctctaaa acctagaaaa agcgacttca cactatagtg agtcgtatta       60

<210> SEQ ID NO 29
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 29
caaaacagca tagctctaaa actctttttt cttttctct atctatagtg agtcgtatta        60

<210> SEQ ID NO 30
<211> LENGTH: 60
<212> TYPE: DNA
<213> ORGANISM: Artificial sequence
<220> FEATURE:
<223> OTHER INFORMATION: synthetic oligonucleotide
```

<400> SEQUENCE: 30
caaaacagca tagctctaaa acttgcgatg tactttcatt gactatagtg agtcgtatta    60

<210> SEQ ID NO 31
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 31
caaaacagca tagctctaaa acgtagtatt tatcggcatc atctatagtg agtcgtatta    60

<210> SEQ ID NO 32
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 32
caaaacagca tagctctaaa acgcgctgct tataccgcta tactatagtg agtcgtatta    60

<210> SEQ ID NO 33
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 33
caaaacagca tagctctaaa actaacaagc acagctacaa aactatagtg agtcgtatta    60

<210> SEQ ID NO 34
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 34
caaaacagca tagctctaaa acaaccgaaa acaaaggcaa gtctatagtg agtcgtatta    60

<210> SEQ ID NO 35
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 35
caaaacagca tagctctaaa acgctaatga aacacctata gcctatagtg agtcgtatta    60

<210> SEQ ID NO 36
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 36
caaaacagca tagctctaaa acgaattgat aatcgctgac atctatagtg agtcgtatta    60

<210> SEQ ID NO 37
<211> LENGTH: 60

```
<212> TYPE: DNA
<213> ORGANISM: Artificial sequence
<220> FEATURE:
<223> OTHER INFORMATION: synthetic oligonucleotide

<400> SEQUENCE: 37
caaaacagca tagctctaaa accaaatata ccgccacccg tactatagtg agtcgtatta      60

<210> SEQ ID NO 38
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 38
caaaacagca tagctctaaa acgtcttgcc tgtttattta aactatagtg agtcgtatta      60

<210> SEQ ID NO 39
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 39
caaaacagca tagctctaaa acaatgatga taaacgtgtc aactatagtg agtcgtatta      60

<210> SEQ ID NO 40
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 40
caaaacagca tagctctaaa acccgcgata cgtttcattc atctatagtg agtcgtatta      60

<210> SEQ ID NO 41
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 41
caaaacagca tagctctaaa actccacatt ggccattatg aactatagtg agtcgtatta      60

<210> SEQ ID NO 42
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 42
caaaacagca tagctctaaa acttagtaat gacaacgttt aactatagtg agtcgtatta      60

<210> SEQ ID NO 43
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 43
```
caaaacagca tagctctaaa acaataacat tggtcgctta gactatagtg agtcgtatta        60

<210> SEQ ID NO 44
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 44
caaaacagca tagctctaaa actgctgctc caggccgctg agctatagtg agtcgtatta        60

<210> SEQ ID NO 45
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 45
caaaacagca tagctctaaa acgattcccc tgcctgtgcg gcctatagtg agtcgtatta        60

<210> SEQ ID NO 46
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 46
caaaacagca tagctctaaa acatctcgaa cagggtctcc ggctatagtg agtcgtatta        60

<210> SEQ ID NO 47
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 47
caaaacagca tagctctaaa acctggcggt agtagtcgcg gactatagtg agtcgtatta        60

<210> SEQ ID NO 48
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 48
caaaacagca tagctctaaa actagcgggc ggtcgtcctt gcctatagtg agtcgtatta        60

<210> SEQ ID NO 49
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 49
caaaacagca tagctctaaa acatggcgct gcaaccgcac agctatagtg agtcgtatta        60

<210> SEQ ID NO 50
<211> LENGTH: 60
<212> TYPE: DNA
<213> ORGANISM: Artificial sequence

```
<220> FEATURE:
<223> OTHER INFORMATION: synthetic oligonucleotide

<400> SEQUENCE: 50
caaaacagca tagctctaaa acgtacaacg tcgtatttta tactatagtg agtcgtatta     60

<210> SEQ ID NO 51
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 51
caaaacagca tagctctaaa acccagctgc aatgcgttac acctatagtg agtcgtatta     60

<210> SEQ ID NO 52
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 52
caaaacagca tagctctaaa actgcttgtt gtgctttaat cgctatagtg agtcgtatta     60

<210> SEQ ID NO 53
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 53
caaaacagca tagctctaaa acgccccgat tgtgtggata atctatagtg agtcgtatta     60

<210> SEQ ID NO 54
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 54
caaaacagca tagctctaaa acaatcgcgc cgctaatccg ggctatagtg agtcgtatta     60

<210> SEQ ID NO 55
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 55
caaaacagca tagctctaaa acaggtcata catagactct tcctatagtg agtcgtatta     60

<210> SEQ ID NO 56
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 56
caaaacagca tagctctaaa acacctacta aagcagttgc tactatagtg agtcgtatta     60
```

<210> SEQ ID NO 57
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 57
caaaacagca tagctctaaa acgaaggctc taactctctt acctatagtg agtcgtatta      60

<210> SEQ ID NO 58
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 58
caaaacagca tagctctaaa acgcaatacc aagtaaaaat cgctatagtg agtcgtatta      60

<210> SEQ ID NO 59
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 59
caaaacagca tagctctaaa accgagtgag acttttcttt tgctatagtg agtcgtatta      60

<210> SEQ ID NO 60
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 60
caaaacagca tagctctaaa acagcgcgct cacattcctg aactatagtg agtcgtatta      60

<210> SEQ ID NO 61
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 61
caaaacagca tagctctaaa acgtacctga gtacccatcc aactatagtg agtcgtatta      60

<210> SEQ ID NO 62
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 62
caaaacagca tagctctaaa acgtgaatct gtttctgtca atctatagtg agtcgtatta      60

<210> SEQ ID NO 63
<211> LENGTH: 60
<212> TYPE: DNA
<213> ORGANISM: Artificial sequence
<220> FEATURE:
<223> OTHER INFORMATION: synthetic oligonucleotide

```
<400> SEQUENCE: 63
caaaacagca tagctctaaa acatgacagc gatgccaaga cgctatagtg agtcgtatta      60

<210> SEQ ID NO 64
<211> LENGTH: 60
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (23)..(42)
<223> OTHER INFORMATION: n is a, c, g, or t

<400> SEQUENCE: 64
caaaacagca tagctctaaa acnnnnnnnn nnnnnnnnnn nnctatagtg agtcgtatta      60
```